US00PP32452P2

(12) United States Plant Patent
Heuger

(10) Patent No.: US PP32,452 P2
(45) Date of Patent: Nov. 10, 2020

(54) ***HELLEBORUS* PLANT NAMED 'COSEH 5600'**

(50) Latin Name: ***Helleborus niger* x *Helleborus* x *hybridus***
Varietal Denomination: COSEH 5600

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,791

(22) Filed: Nov. 29, 2019

(51) Int. Cl.
*A01H 6/72* (2018.01)
*A01H 5/02* (2018.01)

(52) U.S. Cl.
USPC ..... Plt./439

(58) Field of Classification Search
USPC ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'COSEH 5600', characterized by its upright and mounded plant habit; moderately vigorous growth habit; dark green-colored leaves; freely flowering habit; single yellow green, white and purple-colored flowers; and good garden performance.

2 Drawing Sheets

Figure 1:
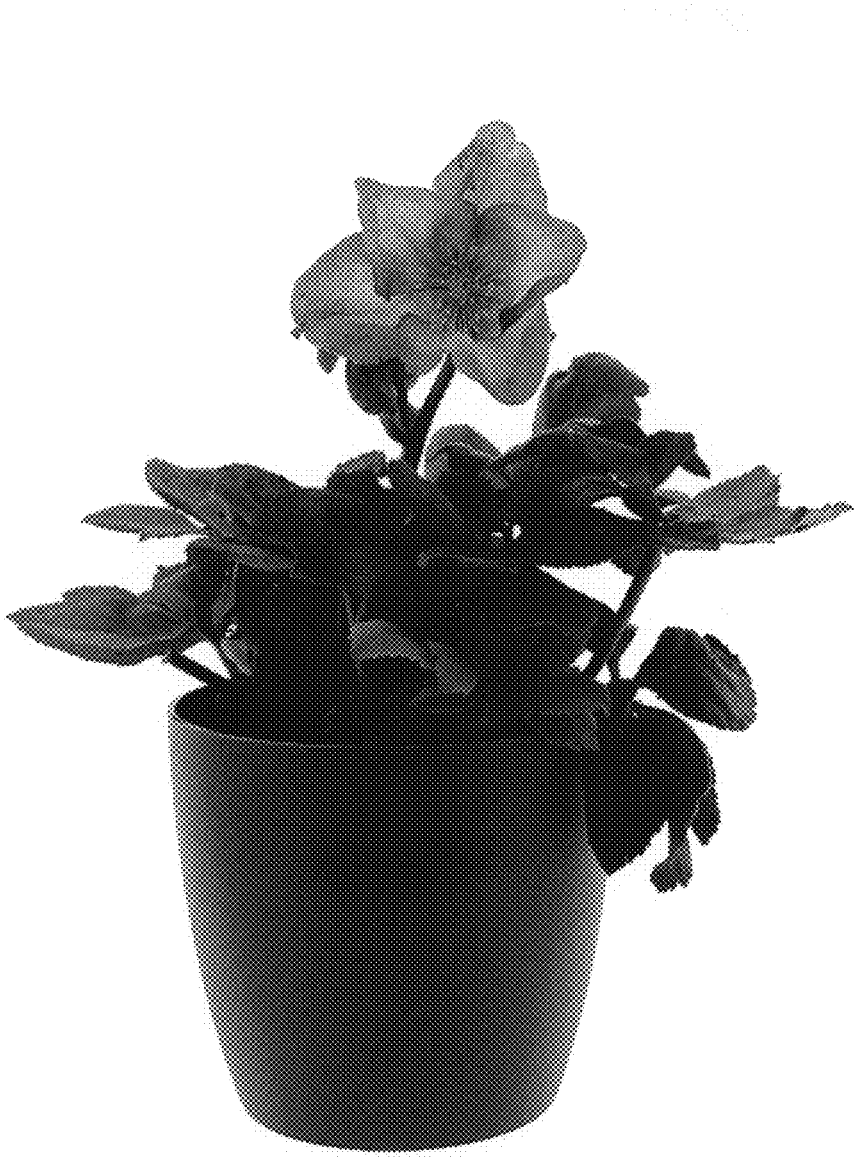

Botanical designation: *Helleborus niger* x *Helleborus* x *hybridus*.

Cultivar denomination: 'COSEH 5600'.

CROSS-REFERENCED TO CLOSELY-RELATED APPLICATIONS

Title: *Helleborus* Plant Named 'COSEH 5700'
Applicant: Josef Heuger
Plant patent application Ser. No. 16/602,738
Title: *Helleborus* Plant Named 'COSEH 5900'
Applicant: Josef Heuger
Plant patent application Ser. No. 16/602,735
Title: *Helleborus* Plant Named 'COSEH 6900'
Applicant: Josef Heuger
Plant patent application Ser. No. 16/602,736
Title: *Helleborus* Plant Named 'COSEH 7100'
Applicant: Josef Heuger
Plant patent application Ser. No. 16/602,734
Title: *Helleborus* Plant Named 'COSEH 7500'
Applicant: Josef Heuger
Plant patent application Ser. No. 16/602,737

BACKGROUND OF THE INVENTION

The present invention relates to a new and distinct cultivar of *Helleborus* plant, botanically known as *Helleborus niger* x *Helleborus* x *hybridus* and hereinafter referred to by the name 'COSEH 5600'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in October, 2011 of a unnamed selection of *Helleborus niger*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2013.

Asexual reproduction of the new *Helleborus* plant by divisions in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5600'. These characteristics in combination distinguish 'COSEH 5600' as a new and distinct *Helleborus* plant:

1. Upright and mounded plant habit.
2. Moderately vigorous growth habit.
3. Dark green-colored leaves.
4. Freely flowering habit.
5. Single yellow green, white and purple-colored flowers.
6. Good garden performance.

Plants of the new *Helleborus* differ from plants of the female parent selection in the following characteristics:

1. Leaves of plants of the new *Helleborus* are darker green than leaves of plants of the female parent selection.
2. Plants of the new *Helleborus* have yellow green, white and purple-colored flowers whereas plants of the female parent selection have white-colored flowers.

Plants of the new *Helleborus* differ from plants of the male parent selection in the following characteristics:

1. Plants of the new *Helleborus* have fewer leaves than plants of the male parent selection.

2. Plants of the new *Helleborus* have yellow green, white and purple-colored darker green-colored flowers whereas plants of the male parent selection have red-colored flowers.

Plants of the new *Helleborus* can be compared to plants of *Helleborus niger* x *Helleborus* x *hybridus* 'COSEH 5700', disclosed in a U.S. Plant Patent application filed concurrently. Plants of the new *Helleborus* differ primarily from plants of 'COSEH 5700' in flower color as plants of the new *Helleborus* have yellow green, white and purple-colored flowers whereas plants of 'COSEH 5700' have red purple-colored flowers.

Plants of the new *Helleborus* can be compared to plants of *Helleborus niger* x *Helleborus* x *hybridus* 'COSEH 5900', disclosed in a U.S. Plant Patent application filed concurrently. Plants of the new *Helleborus* differ primarily from plants of 'COSEH 5900' in flower color as plants of the new *Helleborus* have yellow green, white and purple-colored flowers whereas plants of 'COSEH 5900' have white-colored flowers.

Plants of the new *Helleborus* can be compared to plants of *Helleborus niger* x *Helleborus* x *hybridus* 'COSEH 6900', disclosed in a U.S. Plant Patent application filed concurrently. Plants of the new *Helleborus* differ primarily from plants of 'COSEH 6900' in flower color as plants of the new *Helleborus* have yellow green, white and purple-colored flowers whereas plants of 'COSEH 6900' have light yellow green-colored flowers.

Plants of the new *Helleborus* can be compared to plants of *Helleborus niger* x *Helleborus* x *hybridus* 'COSEH 7100', disclosed in a U.S. Plant Patent application filed concurrently. Plants of the new *Helleborus* differ primarily from plants of 'COSEH 7100' in flower color as plants of the new *Helleborus* have yellow green, white and purple-colored flowers whereas plants of 'COSEH 7100' have red purple-colored flowers.

Plants of the new *Helleborus* can be compared to plants of *Helleborus niger* x *Helleborus* x *hybridus* 'COSEH 7500', disclosed in a U.S. Plant Patent application filed concurrently. Plants of the new *Helleborus* differ primarily from plants of 'COSEH 7500' in flower color as plants of the new *Helleborus* have yellow green, white and purple-colored flowers whereas plants of 'COSEH 7500' have white to light yellow green-colored flowers.

Plants of the new *Helleborus* can also be compared to plants of *Helleborus niger* x *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Leaves of plants of the new *Helleborus* are lighter green in color than leaves of plants of 'LEM 100'.
2. Flowers of plants of the new *Helleborus* are yellow green, white and purple in color whereas flowers of plants of 'LEM 100' are red purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 5600' grown in a container.

Figure 2:
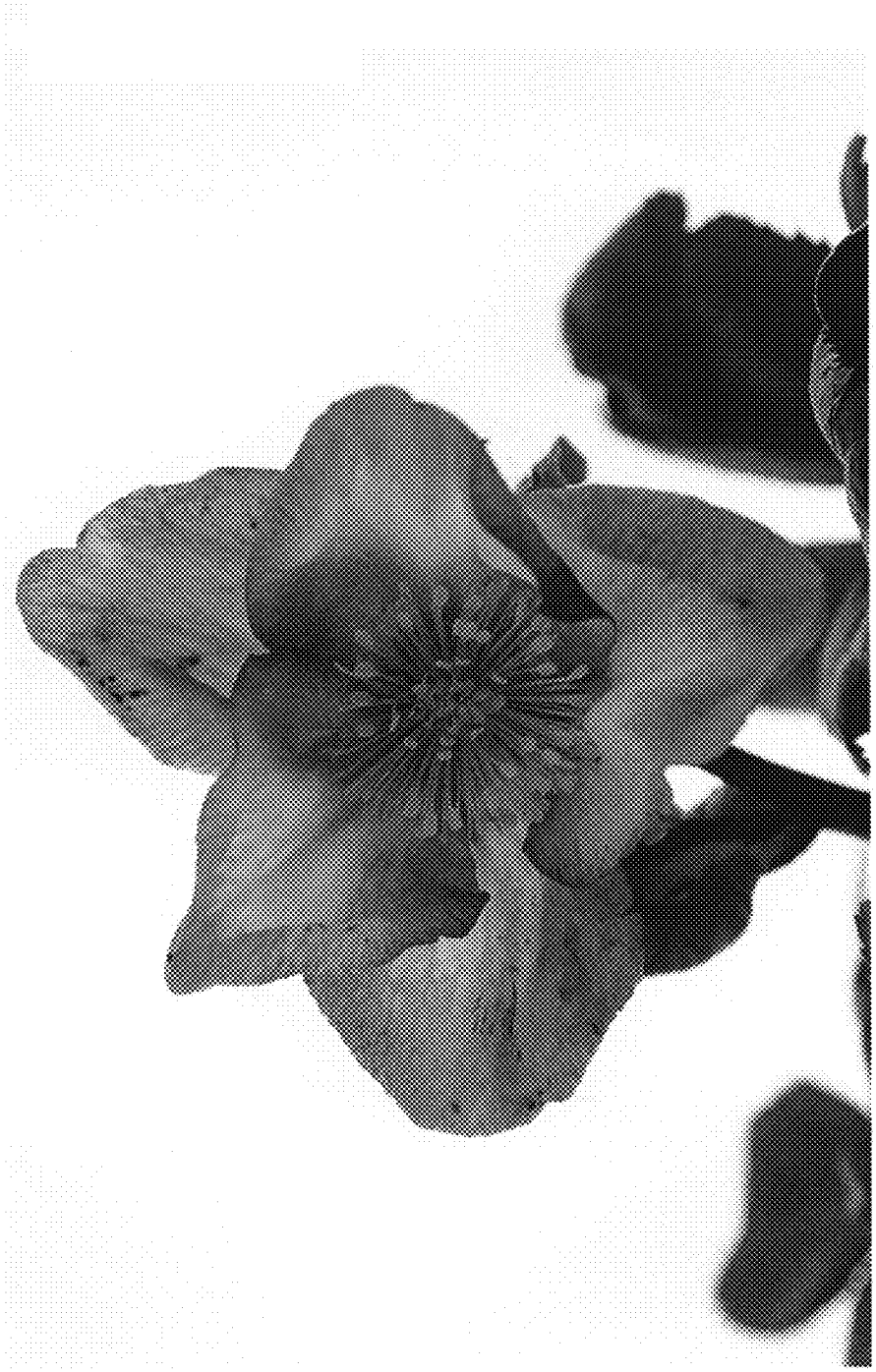

The photograph on the second sheet (FIG. 2 of 2) is a close-up view of a typical flower and leaves of 'COSEH 5600'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* x *Helleborus* x *hybridus* 'COSEH 5600'.

Parentage:

*Female, or seed, parent*.—Unnamed selection of *Helleborus niger*, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly flattened globular; moderately vigorous growth habit and low to moderate growth rate.

*Plant height, soil level to top of foliar plane*.—About 17.6 cm.

*Plant height, soil level to top of flowers*.—About 28.3 cm.

*Plant diameter* (*area of spread*).—About 30.2 cm.

Leaf description:

*Arrangement*.—Leaves arranged in a basal rosette; leaves palmately compound with typically seven or occasionally five leaflets per leaf.

*Leaf length*.—About 12 cm.

*Leaf width*.—About 14.6 cm.

*Leaflet length*.—About 7.5 cm.

*Leaflet width*.—About 4.7 cm.

*Leaf shape*.—Palmate; reniform in outline.

*Leaflet shape*.—Ovate to broadly ovate, broadly elliptic or broadly obovate.

*Leaflet apex*.—Acute.

*Leaflet base*.—Attenuate.

*Leaflet margin*.—Serrate; slightly undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to 137B; midvein tinged proximally, close to 178B. Developing leaflets, lower surface: Close to 147B; midvein tinged with close to 177B. Fully developed leaflets, upper surface: Darker than between 139A and 147A; proximally, close to 200A; venation, close to 147B. Fully developed leaflets, lower surface: Close to 144B; venation, close to 145A.

*Petioles*.—Length: About 10.4 cm. Diameter: About 5.5 mm to 7 mm. Strength: Strong. Texture and luster, upper and lower surfaces: Smooth, glabrous; slightly glossy. Color, upper and lower surfaces: Close to 144B; moderately covered with fine dots, close to 177B and 200A.

Flower description:

*Flower shape and habit*.—Single rotate flowers; flowers slightly to moderately cupped; arranged solitary or in clusters with about six flowers each; freely flowering habit with about 24 flowers developing per plant; flowers face mostly outwardly to slightly nodding or slightly upright.

*Fragrance*.—None detected.

*Natural flowering season*.—Plants begin flowering about ten months after planting; plants flower from the late autumn into the winter in Germany.

*Flower longevity on the plant*.—About three to four months; sepals persistent, other flower parts are not persistent.

*Flower buds*.—Length: About 2.6 cm. Diameter: About 1.3 cm. Shape: Narrowly ovate to ovate. Texture and luster: Smooth, glabrous; matte. Color: Close to between 145C and 157B.

*Inflorescence height*.—About 26.8 cm.

*Inflorescence diameter*.—About 13.6 cm.

*Flower diameter*.—About 8 cm by 8 cm.

*Flower depth* (*height*).—About 2.7 cm.

*Petals*.—All petals are transformed into nectaries.

*Sepals*.—Quantity and arrangement: About five, arranged in a single whorl. Length: About 4.2 cm. Width: About 4.5 cm. Shape: Broadly ovate to close to reniform, slightly concave. Apex: Obtuse. Base: Truncate to rounded. Margin: Entire; slightly undulate. Texture and luster, upper surface: Smooth, glabrous; matte. Texture and luster, lower surface: Smooth, glabrous; matte to slightly glossy. Color: When opening, upper surface: Close to NN155C and distally, close to N155B; towards the margins and venation, close to 75A. When opening, lower surface: Close to NN155B; towards the margins and venation, tinged with close to N74C. Fully opened, upper surface: Close to NN155B to NN155C; towards the margins, close to 75B to 75C; with development, colors becoming closer to 145D and towards the margins and apex, close to 145A; proximally tinged with close to 75B. Fully opened, lower surface: Close to NN155B; towards the margins and venation, close to N74D; with development, colors becoming closer to 144B and 145A and towards the margins and base, tinged with close to 70B and N186D; venation, close to 71A and 71B.

*Flower bracts*.—Quantity per flower: Typically one or two. Length: About 5.6 cm. Width: About 3.3 cm. Shape: Ovate to broadly ovate. Apex: Acute. Base: Truncate. Margin: Distally, shallowly dentate to serrate to serrate; proximally, entire; coarsely undulate. Color, upper surface: Close to 137B; venation, close to 137A. Color, lower surface: Close to 138B; venation, close to 177A to 177B.

*Peduncles*.—Length: About 15.7 cm. Diameter: About 7.5 mm to 8 mm. Aspect: About 15° from vertical. Strength: Strong. Texture and luster: Smooth, glabrous; slightly glossy. Color: Close to 146D; heavily and finely dotted, close to 184A.

*Pedicels*.—Length: About 2.3 cm. Diameter: About 3 mm. Aspect: About 10° from peduncle axis. Strength: Moderately strong. Texture and luster: Smooth, glabrous; moderately glossy. Color: Close to 145A; proximally, tinged with close to 152D.

*Reproductive organs*.—Stamens: Quantity per flower: About 140. Filament length: About 1.6 cm. Filament color: Close to NN155C. Anther shape: Double and broadly reniform; basifixed. Anther size: About 2 mm by 2 mm. Anther color: Close to 150C. Pollen amount: Scarce to moderate. Pollen color: Close to 4D. Pistils: Quantity per flower: About seven to ten. Pistil length: About 1 cm. Stigma diameter: About 0.3 mm. Stigma shape: Club-shaped. Stigma color: Close to 150D. Style length: About 9 mm. Style color: Close to 63C; proximally, close to 69D. Ovary color: Close to 150D. Nectaries (transformed petals): Quantity per flower: About 13. Length: About 1 cm. Diameter: About 3 mm. Shape: Tubular, moderately flattened. Texture and luster, inner and outer surfaces: Smooth, glabrous; slightly glossy. Color, immature, inner and outer surfaces: Close to 144B and towards the base, close to 146D. Color, mature, inner and outer surfaces: Close to 144C, distally, close to 144D and proximally, close to 146D; with development, close to 144C, distally, close to 145C and proximally, close to 146D.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5600' as illustrated and described.

* * * * *